United States Patent [19]

Hargis

[11]  4,261,865
[45]  Apr. 14, 1981

[54] CATALYST FOR OLEFIN PRODUCTION
[75] Inventor: Duane C. Hargis, Pleasant Ridge, Mich.
[73] Assignee: Ethyl Corporation, Richmond, Va.
[21] Appl. No.: 91,722
[22] Filed: Nov. 6, 1979
[51] Int. Cl.³ .......................... B01J 21/06; B01J 23/78
[52] U.S. Cl. .................................................. 252/474
[58] Field of Search ........................ 252/474; 423/598
[56] References Cited
U.S. PATENT DOCUMENTS
2,729,664  1/1956  Kirshenbaum ................... 252/474 X
2,731,486  1/1956  Rottig .............................. 252/474 X Primary Examiner—W. J. Shine
Attorney, Agent, or Firm—Donald L. Johnson; Joseph D. Odenweller; Willard G. Montgomery

[57]  ABSTRACT

A process for selectively preparing alpha-olefins having from 2 to about 22 carbon atoms by contacting a gaseous mixture containing carbon monoxide and hydrogen with an iron titanate-alkali metal hydroxide catalyst at reaction conditions correlated so as to favor the formation of a substantial proportion of such alpha-olefin product.

3 Claims, No Drawings

CATALYST FOR OLEFIN PRODUCTION

BACKGROUND OF THE INVENTION

This invention relates to a Fischer-Tropsch reaction. More particularly, this invention relates to the reaction between carbon monoxide and hydrogen in the presence of an iron titanate catalyst in combination with an alkali metal hydroxide to selectively produce alpha-olefins under reaction conditions correlated to produce such olefin product.

It is well known that valuable organic compounds may be produced by the catalytic hydrogenation, under pressure, of oxides of carbon, particularly carbon monoxide. The prior art is replete with numerous metallic catalysts which have been utilized, both in supported and non-supported forms. Efforts to convert synthesis gas (i.e. carbon monoxide and hydrogen) into a definitive class of products, however, has not been readily accomplished. Most synthesis gas conversion processes generally tend to give a wide spectrum of products, for example, hydrocarbons and oxygenated hydrocarbons having a broad distribution of carbon atom contents. Alpha-olefins, particularly alpha-olefins having from 6 to 12 carbon atoms are particularly useful in the synthetic chemical industry finding uses, for example, as intermediates for alcohol synthesis and as detergents in lube oil and fuel compositions. Heretofore, these olefins have been commercially obtained principally from the polymerization of lower olefins produced by the thermal decomposition of petroleum fractions and natural gas. Accordingly, with the decline of available reserves of natural gas and petroleum crude, it is highly desirable to find alternative means for producing such olefins which are not dependent upon natural gas and petroleum feedstock.

It is therefore an object of the present invention to provide a process for the selective conversion of synthesis gas into alpha-olefin products.

It is another object of the present invention to provide an iron titanate-alkali metal hydroxide catalyst which is highly reactive and highly selective for converting synthesis gas into alpha-olefin products.

Other objects and advantages of the present invention shall become apparent from the accompanying description and examples.

SUMMARY OF THE INVENTION

The present invention provides a method for selectively producing alpha-olefins having from 2 to about 22 carbon atoms from gaseous mixtures of carbon monoxide and hydrogen using an iron titanate-alkali metal hydroxide catalyst.

DESCRIPTION OF THE PREFERRED EMBODIMENT

This is achieved by contacting, in a reaction zone, a gaseous mixture of carbon monoxide and hydrogen with a catalyst comprising solid particles of iron titanate which have been treated with an alkali metal hydroxide at reaction conditions correlated to produce such alpha-olefin product. Thus, a preferred embodiment of the present invention is a process for selectively producing alpha-olefins having from 2 to about 22 carbon atoms which comprises the step of contacting a gaseous mixture containing carbon monoxide and hydrogen with a catalyst comprising iron titanate and an alkali metal hydroxide at reaction conditions correlated so as to favor the formation of a substantial proportion of such alpha-olefin product.

The catalyst used in the practice of this invention is believed novel and its constituents different from those of the prior art. By use of the catalyst according to this invention, it is possible to carry out the reduction of carbon monoxide to obtain a mixture of alpha-olefins having from 2 to about 22 carbon atoms. The catalyst according to this invention comprises solid particles of iron titanate which have been treated with an alkali metal hydroxide. Thus, another embodiment of the present invention is a catalyst for converting gaseous mixtures of carbon monoxide and hydrogen to alpha-olefins having from 2 to about 22 carbon atoms said catalyst comprising iron titanate and an alkali metal hydroxide.

PROCESS DISCUSSION

The reaction is conducted at more or less conventional Fischer-Tropsch reaction conditions of temperature, pressure, gas composition, and space velocity so that conventional technology and equipment may be used. Over all, the reaction is conducted at reactive conditions of temperature, pressure, gas composition and space velocity which are correlated to achieve optimal selectivity for alpha-olefins. The reaction efficiency, or selectivity, to alpha-olefins is invariably at least about 35% and is usually upwards of about 45%. Under preferred conditions it exceeds 50% and, under optimum conditions, can reach 60% or more excluding carbon dioxide from the product. Selectivity is defined herein as the percentage of carbon atoms converted from carbon monoxide to a specified compound or compounds other than carbon dioxide.

The reaction is highly exothermic with the thermodynamic equilibria and the kinetic reaction rates being governed by the reaction temperature. Average catalyst bed temperatures are usually within the range of about 200° C.–300° C., but for optimum conversions, bed temperatures are kept within the range of about 225° C. to about 275° C., typically about 225° C. to 250° C.

The reaction temperature appears to be an important process variable affecting not only total productivity, but selectivity towards the desired alpha-olefin products. For example, it has been determined that a temperature change of approximately 25° C. from about 225° C. to 250° C., with all other variables being constant, increases total synthesis gas conversion and tends to increase the efficiency of alpha-olefin production. On the other hand, however, temperatures higher than approximately 275° C. tend to increase the production of lighter hydrocarbons, i.e. $C_2$–$C_4$ olefins and methane at the expense of the higher olefins.

In the above discussion, the indicated temperatures are expressed as average, or mean, reaction bed temperatures. Because of the tendencies to produce increased amounts of lighter olefins at higher reaction temperatures, it is desirable for the purposes of the present invention that for optimal selectivity to long chain ($>C_5$ olefin) alpha-olefin production that temperatures be controlled so as not to exeed about 275° C.

The reaction zone pressure is desirably within the range of about 50 psig to about 250 psig. A reaction zone pressure of approximately 225 psig is preferred. Activity, however, can be achieved at atmospheric pressure. In general, with all other variables held constant, as pressure decreases, from 225 psig to 0 psig, production of lighter olefins, alcohols and methane increases while higher olefin production (>$C_5$) decreases. Also as pressure decreases, conversion decreases. $CO_2$ production is relatively unaffected when pressure is decreased from 250 psig to atmospheric. Olefin distribution, however, is affected by changing reaction pressure. For example, excluding the lighter olefins, i.e. $C_2$–$C_4$, and with all other variables being held constant, it has been determined that at 225 psig, olefin distribution peaks at $C_5$–$C_6$; at approximately 60 psig distribution peaks in the range of $C_6$–$C_{10}$; and at atmospheric pressure distribution peaks at $C_7$–$C_{12}$.

The ratio of hydrogen to carbon monoxide in the synthesis gas may vary somewhat. Normally, the mole ratio of hydrogen to carbon monoxide is within the range of 2:1 to 1:2. Preferably, the mole ratio of hydrogen to carbon monoxide is 1:1. Generally, increasing the amount of hydrogen in the gaseous mixture tends to increase the total rate of reaction.

Conversion is conveniently achieved by employing a high space velocity correlated with other reaction variables (e.g. temperature, pressure, gas composition, catalyst, etc.,). Space velocity of from about 1200 to 2400 gas hourly space velocities (volumes of reactant gas at 0° C. and 760 mm mercury pressure, per volume of catalyst per hour) are generally employed. A preferred gas hourly space velocity is approximately 1200 GHSV.

A highly preferred embodiment of the present invention is a process for producing alpha-olefins having from 2 to about 22 carbon atoms comprising contacting a gaseous mixture of carbon monoxide and hydrogen with a catalyst comprising iron titanate and an alkali metal hydroxide at reaction conditions correlated to produce such alpha-olefin product, said reaction conditions including a temperature within the range of from about 225° C. to 275° C., a pressure within the range of about 225–250 psig, and a mole ratio of hydrogen to carbon monoxide of 1:1.

THE CATALYST

The catalyst of iron titanate and alkali metal hydroxide is provided in the reaction zone as particles, such as placing particles of iron titanate which have been treated with an alkali metal hydroxide in the reaction zone, generally supported by an inert porous packing material, such as, for example, glass wool. Another way is to deposit the catalyst particles in a basket-like container in the reaction zone. The catalysts of the present invention are all prepared by essentially the same sequence of steps. An aqueous solution of an alkali metal hydroxide is added to a beaker containing particles of iron titanate. Potassium hydroxide has been found to be a particularly effective alkali metal hydroxide for use in the practice of the present invention. The fact that potassium hydroxide has proven to be effective would appear to indicate that other alkali and/or alkaline earth metal hydroxides may also be used in the practice of the present invention. Generally, from about 0.1 weight percent to about 3.0 weight percent of alkali metal hydroxide based on the total weight of the catalyst composition is preferred. Especially preferred is an iron titanate-alkali metal hydroxide catalyst composition containing from about 0.2 weight percent to about 1.0 weight percent of the alkali metal hydroxide. Generally, as the amount of alkali metal hydroxide in the catalyst composition increases up to approximately 3.0 weight percent, reactivity and selectivity for alpha-olefin product also increases. However, the presence of alkali metal hydroxide in an amount greater than 3.0 weight percent in the composition appears to result in reduced activity although selectively appears to remain substantially unaffected. In preparing the catalyst composition of the present invention, the amount of alkali metal hydroxide solution added to the iron titanate particles is an amount sufficient only to completely wet the iron titanate particles and no more. Typically, 5 ml of a 40% solution of alkali metal hydroxide in distilled water is used. This technique of catalyst preparation is well known and is commonly referred to as the incipient wetness technique. By contacting the solid particles of iron titanate with just enough alkali metal hydroxide solution to merely wet the iron titanate particles with little or no excess solution being used insures that the desired concentration of alkali metal hydroxide will be incorporated into the catalyst composition. After treating the particles of iron titanate with the alkali metal hydroxide solution, the catalyst material is subjected to drying conditions to lower the water content of the resultant catalyst composition to the lowest possible level. In a typical drying procedure, the catalyst composition is slowly heated from room temperature up to a temperature of approximately 100° C. and is maintained at this temperature for a period of time of at least one hour until substantially all of the water content of the catalyst composition is removed.

As a further required step in the procedure for catalyst production, the dry-state catalyst composition is reduced with hydrogen. It has been found advantageous to conduct the reduction of the catalyst composition by contacting the catalyst composition in a reduction zone with hydrogen, and then heating the catalyst reduction zone slowly from room temperature up to approximately 300° C. It is highly preferred that the catalyst reduction zone be maintained at this temperature for approximately 18 to 24 hours in order to effect reduction of the catalyst composition. For the purposes of the present invention, it appears that complete reduction of iron to the zero valent state is not desirable for optimal production of long chain alpha-olefins.

TEST REACTOR

The reactor used in the practice of the present invention is a stainless steel tube of 0.305 in. internal diameter, 0.375 in. outside wall diameter with a wall thickness of 0.035 in. The length is 14 inches and the reactor capacity is approximately 16.5 ml. The tube is packed with a catalyst prepared as described above deposited on a glass wool support. Carbon monoxide and hydrogen are fed to the reactor in the desired mole ratio from 1750 psig headers. Typically, 5 ml of catalyst are placed in the reactor on the support. The reactor is then pressurized with hydrogen and the flow of carbon monoxide and hydrogen are adjusted to achieve the desired composition. During pressurization of the reactor, the reactor temperature and pressure are adjusted to reaction conditions. At least 5 to 6 hours are allowed for the reactor to come to a steady state before beginning to measure actual time of reaction. The reaction is then allowed to proceed for approximately 24 hours after which a sample of liquid product is collected by cooling the product containing gas through a cold water condenser at approximately 225 psig and then trapping the liquid product in a dry ice-acetone trap having a capacity of approximately 55 cc. The liquid product from the trap and the condenser are then combined to obtain a single liquid sample which is then analyzed by gas chromatography. The non-condensable gases are metered through a wet-test meter to determine the volume of gas, and a gas sample is collected to determine its composition.

The following examples serve to provide specific illustrations of the present invention.

EXAMPLE 1

This example illustrates the preparation of the iron titanate-alkali metal hydroxide catalyst of the present invention.

8.30 grams of iron titanate particles (100 mesh), obtained commercially from Cerac, Inc., 407 North 13th Street, Milwaukee, Wis., were deposited in a 50 ml beaker. Next, 0.083 grams of potassium hydroxide dissolved in an amount of distilled water (typically 5 ml) were added to the iron titanate particles in the beaker. This produced a catalyst composition containing 1.0 weight percent potassium hydroxide. The composition was then heated slowly from room temperature to a temperature of about 100° C. and dried at this temperature for approximately one hour to remove substantially all of the water from the composition. The dried catalyst composition was then placed in the reactor, aforedescribed, on an inert packing support and reduced with hydrogen. This was accomplished by slowly heating the catalyst from room temperature to a temperature of approximately 300° C. while flowing 50 ml per hour of hydrogen over the catalyst. Contact of the catalyst with hydrogen was continued at these conditions for approximately 18 hours.

EXAMPLE 2

This example compares the effect of alkali metal hydroxide loading on the selectivity of the iron titanate-alkali metal hydroxide catalyst for alpha-olefin products.

8.3 grams of untreated iron titanate particles (100 mesh) were deposited in the reactor apparatus described in the TEST REACTOR section. The sample was then reduced in hydrogen at 300° C. for approximately 18 hours. Reaction conditions are summarized below.

Temperature: 250° C.
Pressure: 225 psig
Volume Hourly Space Velocity: 1200 hr.$^{-1}$
$H_2/CO$ Molar Ratio: 1:1

The carbon monoxide conversion was found after several hours on stream to be 3.0 mole percent. The carbon monoxide conversion is defined as 100 times the moles of carbon monoxide converted divided by the moles of carbon monoxide in the feedstock. The reaction product consisted of:

| Distribution, C% | |
|---|---|
| $CO_2$ | 21.1 |
| $CH_4$ | 23.9 |
| $C_2$—$C_4$ paraffinic | 4.1 |
| $C_5$—$C_{22}$ paraffinic | 14.4 |
| $C_2$—$C_4$ olefin | 11.7 |
| $C_5$—$C_{22}$ olefin | 7.9 |
| $C_5$—$C_{22}$ alcohol | 3.2 |
| Other Hydrocarbons | 4.8 |
| Aqueous Oxygenates | 9.0 |

For comparison, an iron titanate-potassium hydroxide catalyst composition containing 1.0 weight percent potassium hydroxide prepared as described in Example 1 was deposited in the reactor and reduced in hydrogen at 300° C. for approximately 18 hours in the same manner as the untreated iron titanate catalyst described above. A synthesis gas conversion run using the iron titanate-potassium hydroxide catalyst was then carried out under the same reaction conditions used in the aforedescribed run for the untreated iron titanate catalyst. Analysis of the reaction product showed the following:

| Distribution, C% | |
|---|---|
| $CO_2$ | 54.2 |
| $CH_4$ | 2.9 |
| $C_2$—$C_4$ paraffinic | 0.9 |
| $C_5$—$C_{22}$ paraffinic | 3.3 |
| $C_2$—$C_4$ olefin | 5.9 |
| $C_5$—$C_{22}$ olefin | 21.9 |
| $C_5$—$C_{22}$ alcohol | 4.1 |
| Other Hydrocarbons | 5.4 |
| Aqueous Oxygenates | 0.7 |

A comparison of the distribution between the alkali metal hydroxide treated iron titanate catalyst and the untreated catalyst, excluding $CO_2$ from the reaction product reveals:

| | Distribution Excluding $CO_2$ | |
|---|---|---|
| | $Fe_2TiO_5$ | $Fe_2TiO_5$ + 1% KOH |
| $CH_4$ | 30.3 | 6.4 |
| $C_2$—$C_4$ paraffinic | 5.2 | 2.0 |
| $C_5$—$C_{22}$ paraffinic | 18.2 | 7.3 |
| $C_2$—$C_4$ olefin | 14.8 | 13.1 |
| $C_5$—$C_{22}$ olefin | 10.0 | 48.6 |
| $C_5$—$C_{22}$ alcohol | 4.1 | 9.1 |
| Other Hydrocarbons | 6.1 | 12.0 |
| Aqueous Oxygenates | 11.4 | 1.6 |

As shown by the foregoing data, the Fischer-Tropsch type product produced by the untreated iron titanate catalyst was mostly paraffinic in nature—especially the long chain fraction (>$C_5$). The addition of 1.0 weight percent potassium hydroxide to the iron titanate, however, increased the activity and significantly altered product selectivity. At 250° C., carbon monoxide conversion increased from 3.0% for the untreated catalyst to approximately 50% for the alkali metal hydroxide treated catalyst. The $CO_2$ yield doubled, production of light hydrocarbons decreased markedly and the long chain products were mostly alpha-olefins. If $CO_2$ is excluded from the product, alpha-olefins comprise over 60% of the organic product formed.

EXAMPLE 3

A series of runs were made to determine the effects of temperature, $H_2/CO$ ratio, and space velocity on the reaction of synthesis gas over an iron titanate-alkali metal hydroxide catalyst containing 1.0 weight percent potassium hydroxide. Temperature was varied from 200° C. to 250° C.; $H_2/CO$ ratio was varied from 0.5 to 2.0 and space velocity was varied from 1200 to 2400 hr.$^{-1}$ The catalyst used in these runs was prepared according to the procedure set forth in preceeding Example 1 above. The test reactor and the procedure described in the foregoing TEST REACTOR and PROCESS DISCUSSION sections were used. Reaction conditions and product composition data are summarized as Run Nos. 1–8 in the Table I below.

TABLE 1

SYN GAS REACTION OVER Fe$_2$TiO$_5$-1% KOH CATALYST

| Run | 1 | 2 | 3 | 4 | 5 | 6 | 7 | 8 |
|---|---|---|---|---|---|---|---|---|
| H2/CO | 1.0 | 0.5 | 1.0 | 2.0 | 0.5 | 1.0 | 2.0 | 1.0 |
| GHSV | 1200 | 1200 | 1200 | 1200 | 1200 | 1200 | 1200 | 2400 |
| Temp, °C. | 200 | 225 | 225 | 225 | 250 | 250 | 250 | 250 |
| g organic/day | .09 | .46 | .57 | .90 | .78 | 2.49 | 3.97 | 1.90 |
| CO Conv., % | .41 | 1.7 | 3.0 | 7.4 | 4.0 | 14.9 | 32.2 | 6.0 |
| Distribution, C% | | | | | | | | |
| CO$_2$ | 50.1 | 56.8 | 60.1 | 60.0 | 68.9 | 59.6 | 53.4 | 67.2 |
| CH$_4$ | | 2.1 | 3.1 | 4.2 | 4.2 | 4.7 | 4.3 | 4.7 |
| C$_2$—C$_3$ Hyd. | | | | | 7.2 | 7.2 | 7.0 | 6.7 |
| Oil | 48.6 | 40.5 | 35.3 | 34.0 | 18.8 | 27.4 | 33.3 | 19.4 |
| Oxygenates | 1.3 | .6 | 1.5 | 1.8 | 1.0 | 1.1 | 1.9 | 2.1 |
| Distribution, C% Excluding CO$_2$ | | | | | | | | |
| CH$_4$ | 4.9 | 7.8 | 10.5 | 13.5 | 11.6 | 9.2 | 14.3 | |
| C$_2$—C$_3$ Hyd | | | | | 23.1 | 17.8 | 15.1 | 20.4 |
| Oil | 97.4 | 93.8 | 88.5 | 85.0 | 60.3 | 67.8 | 71.6 | 59.0 |
| Oxygenates | 2.6 | 1.4 | 3.8 | 4.5 | 3.2 | 2.7 | 4.1 | 6.4 |
| Oil Layer Distribution wt% | | | | | | | | |
| α-olefins | 15.1 | 38.1 | 40.6 | 40.1 | 49.9 | 47.9 | 54.7 | 43.6 |
| n-paraffins | 23.0 | 11.3 | 13.1 | 10.2 | 12.9 | 14.4 | 14.7 | 13.0 |
| p-alcohols | 14.3 | 20.8 | 21.7 | 23.2 | 18.8 | 21.5 | 24.5 | 21.7 |
| Other | 47.6 | 29.8 | 24.6 | 26.5 | 18.4 | 16.2 | 6.1 | 21.7 |

As shown by the data in Table 1 above, in general—within the reaction parameters chosen—low temperatures; high hydrogen content in the synthesis gas, and low space velocity favor the formation of long chain alpha-olefins. CO$_2$ formation is relatively unaffected by the variables tested.

EXAMPLE 4

This example compares the effect of increasing alkali metal hydroxide loading from 0.1 to 1.0 weight percent on the activity and selectivity of the iron titanate-alkali metal hydroxide catalyst of the instant invention. A total of 4 runs were made using the reactor and procedure aforedescribed in the TEST REACTOR and PROCESS DISCUSSION sections. The amount of loading was varied from 0.1 weight percent potassium hydroxide to 1.0 weight percent potassium hydroxide. All catalysts were prepared as described in preceeding Example 1. Reaction conditions and product composition data are summarized in Run Nos. 1-4 in Table 2 below.

TABLE 2

EFFECT OF KOH LOADING ON Fe$_2$TiO$_5$ CATALYSTS

| KOH, wt% | 0 | .11 | .30 | 1.0 |
|---|---|---|---|---|
| H$_2$/CO | 1.0 | 1.0 | 1.0 | 1.0 |
| Temp, °C. | 250 | 300 | 250 | 250 |
| g organic/day | 1.22 | 1.84 | 3.94 | 2.49 |
| CO Conv, % | 3.0 | 9.3 | 20.5 | 14.9 |
| Distribution, C% | | | | |
| CO$_2$ | 21.1 | 58.8 | 59.3 | 59.6 |
| CH$_4$ | 23.9 | 9.9 | 5.0 | 4.7 |
| C$_2$—C$_3$ Hyd. | 15.8 | 14.7 | 11.6 | 7.2 |
| Oil | 30.3 | 15.2 | 22.2 | 27.4 |
| Oxygenates | 9.0 | 1.4 | 1.9 | 1.1 |
| Distribution, C% Excluding CO$_2$ | | | | |
| CH$_4$ | 30.3 | 24.0 | 12.3 | 11.6 |
| C$_2$—C$_3$ Hyd | 20.0 | 35.7 | 28.5 | 17.8 |
| Oil | 38.4 | 36.9 | 54.5 | 67.8 |
| Oxygenates | 11.4 | 3.5 | 4.7 | 2.7 |
| Oil Layer Distribution, wt% | | | | |
| α-olefins | 26.0 | 61.0 | 54.7 | 48.0 |
| n-paraffins | 47.5 | 9.7 | 15.2 | 12.5 |
| p-alcohols | 10.7 | 11.4 | 20.3 | 20.6 |
| Other | 15.8 | 17.9 | 9.8 | 18.9 |

As shown in Table 2 above at 0.1 weight percent potassium hydroxide, catalyst activity at 250° C. was less than that for untreated iron titanate; 0.1% verses 3.0% carbon monoxide conversion (confer Example 2). At 0.3 weight percent and 1.0 weight percent potassium hydroxide good activity was obtained at 250° C. As the potassium hydroxide loading increased from 0.1 to 1.0 weight percent, the product distribution changed as follows:

Light hydrocarbon (C$_1$-C$_3$) decreased
Heavy Hydrocarbons (>C$_5$) increased
Alpha-Olefin in oil product decreased
Alcohols in oil product increased
CO$_2$ was unaffected
Alpha-Olefin distribution was unchanged From the foregoing data it appears that potassium hydroxide concentrations from about 0.2 to 0.5 weight percent appear to optimize alpha-olefin production.

Claims to the invention follow.

I claim:

1. A catalyst composition for converting gaseous mixtures containing carbon monoxide and hydrogen to alpha-olefins having from 2 to about 22 carbon atoms, said catalyst comprising iron titanate and an alkali metal hydroxide which has been reduced with hydrogen.

2. The composition of claim 1 wherein the amount of alkali metal hydroxide ranges from about 0.1 weight percent to about 3.0 weight percent based on the total weight of the composition.

3. The composition of claim 2 wherein said alkali metal hydroxide is potassium hydroxide.

* * * * *